(12) United States Patent
Singh

(10) Patent No.: US 8,017,623 B2
(45) Date of Patent: Sep. 13, 2011

(54) DEXTROMETHORPHAN HYDROCHLORIDE

(75) Inventor: Chandra Singh, San Antonio, TX (US)

(73) Assignee: Trinity Laboratories, Inc., San Antonio, TX (US)

( * ) Notice: Subject to any disclaimer, the term of this patent is extended or adjusted under 35 U.S.C. 154(b) by 344 days.

(21) Appl. No.: 12/167,778

(22) Filed: Jul. 3, 2008

(65) Prior Publication Data

US 2010/0004278 A1 Jan. 7, 2010

(51) Int. Cl.
*A61K 31/44* (2006.01)
(52) U.S. Cl. ...................................................... 514/286
(58) Field of Classification Search .................... 514/286
See application file for complete search history.

(56) References Cited

U.S. PATENT DOCUMENTS

2004/0185097 A1* 9/2004 Kannan et al. ................ 424/468

OTHER PUBLICATIONS

Abraham et al., "Dextromethorphan mitigates phantom pain in cancer amputees," *Annals of Surgical Oncology*, 10:268-274, 2003.
Bem and Peck, "Dextromethorphan. An overview of safety issues," *Drug. Saf.*, 7:190-9, 1992.
Char et al., "Nasal delivery of [14C]dextromethorphan hydrochloride in rats: levels in plasma and brain," *J. Pharm. Sci.*, 81:750-752, 1992.
Gilron et al., "A randomized, controlled trial of high-dose dextromethorphan in facial neuralgias," *Neurology*, 55:964-71, 2000.
Henderson et al., "Perioperative dextromethorphan reduces postoperative pain after hysterectomy," *Anesth. Analg.*, 89:399-402, 1999.
Panitch et al., "Randomized, controlled trial of dextromethorphan/quinidine for pseudobulbar affect in multiple sclerosis," *Ann. Neurol.*, 59:780-787, 2006.
Rauws and van Logten, "The influence of dietary chloride on bromide excretion in the rat," *Toxicology*, 3:29-32, 1975.
Rauws, "Pharmacokinetics of bromide ion—an overview," *Fd. Chem. Toxic.*, 21:379-382, 1983.
Sang et al., "Dextromethorphan and memantine in painful diabetic neuropathy and postherpetic neuralgia: efficacy and dose-response trials," *Anesthesiology*, 96:1053-61, 2002.
Sangster et al., "The influence of sodium bromide in man: a study in human volunteers with special emphasis on the endocrine and the central nervous system," *Fd. Chem. Toxic.*, 21:409-419, 1983.
Sindrup and Jensen, "Efficacy of pharmacological treatments of neuropathic pain: an update and effect related to mechanism of drug action," *Pain*, 83:389-400, 1999.
Steinberg et al., "Dose escalation safety and tolerance study of the N-methyl-D-aspartate antagonist dextromethorphan in neurosurgery patients," *J. Neurosurg.*, 84:860-866, 1996.
Tortella et al., "Dextromethorphan and neuromodulation: old drug coughs up new activities," *Trends Pharmacol. Sci.*, 10:501-507, 1989.
van Logten et al., "Semichronic toxicity studies of sodium bromide in rats on a normal diet and a low chloride diet," *Med. Fac. Landbouw. Rijksuniv. Gent.*, 41/2, 1499-1507, 1976.
Ziemann et al., "Dextromethorphan decreases the excitability of the human motor cortex," *Neurology*, 51:1320-4, 1998.

\* cited by examiner

*Primary Examiner* — Raymond Henley, III
(74) *Attorney, Agent, or Firm* — Nevrivy Patent Law Group P.L.L.C.

(57) ABSTRACT

The present invention provides pharmaceutical compositions comprising dextromethorphan hydrochloride.

9 Claims, 1 Drawing Sheet

DEXTROMETHORPHAN HYDROCHLORIDE

BACKGROUND OF THE INVENTION

Dextromethorphan is a white powder and is available primarily in tablet, capsule and liquid form. The chemical name is 3-methoxy-17-methyl-9a, 13a, 14 a-morphinan with the molecular weight of 271.40 and a molecular formula of $C_{18}H_{25}NO$. Its salt is also known as dextromethorphan hydrobromide, widely used through out the world in hundreds of pharmaceutical preparations and present in preparations such as Anaplex-DM®, Diabe-Tuss DM™, Benylin®, Pertussin®, Delsym®, Sucrets®, Bromfed-DM®, Robitussin®, Vicks Formula 44, etc. Dextromethorphan is a synthetic analog of codeine and d-isomer of 3-methoxy-N-methymorphinan.

It is available as lozenges, capsules, tablets, and cough syrups, in a variety of prescription medications and over-the-counter cough and cold remedies. Products contain dextromethorphan alone or in combination with guaifenesin, brompheniramine, pseudoephedrine, phenylephrine, promethazine, codeine, acetaminophen, and/or chlorpheniramine. For example, Diabe-Tuss DM™ syrup contains 15 mg dextromethorphan Hydrobromide; Benylin® Adult and Pediatric contain 15 mg and 7.5 mg dextromethorphan Hydrobromide, respectively; and Anaplex-DM® contains 30 mg dextromethorphan Hydrobromide, 4 mg brompheniramine and 60 mg pseudoephedrine.

Dextromethorphan is an antitussive agent and, unlike the isomeric levorphanol, it has no analgesic or addictive properties. The drug acts centrally and elevates the threshold for coughing. It is about equal to codeine in depressing the cough reflex. In therapeutic dosage dextromethorphan does not inhibit ciliary activity. It is proposed that dextromethorphan is a glutamate and NMDA antagonist, and blocks the dopamine reuptake site. It may also increase 5HT-1A activity possibly via NMDA antagonism.

Dextromethorphan is rapidly absorbed from the gastrointestinal tract and exerts its effect in 15 to 30 minutes. The duration of action after oral administration is approximately three to six hours. Dextromethorphan is metabolized primarily by liver enzymes undergoing O-demethylation, N-demethylation, and partial conjugation with glucuronic acid and sulfate. In humans, (+)-3-hydroxy-N-methyl-morphinan, (+)-3-hydroxymorphinan, and traces of unmetabolized drug were found in urine after oral administration. The cytochrome P450-2D6 isoenzyme is responsible for the conversion of dextromethorphan to dextrorphan; and P450-3A4 and 3A5 isoenzymes are responsible for converting dextromethorphan to 3-methoxymorphinan and 3-hydroxymorphinan. Potential inhibitors of these isoenzymes could decrease the rate of dextromethorphan elimination if administered concurrently, while potential inducers could increase the rate of elimination.

A single 20 mg oral dose of dextromethorphan produced peak concentrations of 1.8 ng/mL in serum after 2.5 hours. Chronic oral dosing of 120 mg daily, in divided doses, resulted in peak plasma dextromethorphan concentrations of 0.5-5.9 ng/mL (mean 2.4 ng/mL) in extensive metabolizers, and 182-231 ng/mL (mean 207 ng/mL) in poor metabolizers.

In a 24 hour period, less than 2.5% of a dose is excreted unchanged in the urine, while up to 30% of the conjugated dextrorphan is excreted.

Dextromethorphan Hydrobromide is administered orally. As an antitussive, the recommended dosage for adults and children aged 12 years and older is 60-120 mg daily in divided doses; for children aged 6-12 years, 30-60 mg daily in divided doses; and for children aged 2-6 years, 15-30 mg daily in divided doses. Each brand contains different quantities of dextromethorphan hydrobromide, generally 20-30 mg per dose, and the majority contain other drugs as previously mentioned. Approximate doses are: threshold dose 80-90 mg; light 100-200 mg; common 200-400 mg; strong 400-600; and heavy dose 600-1500 mg.

At recommended doses, dextromethorphan hydrobromide produces little or no CNS depression. At higher doses, positive effects may include acute euphoria, elevated mood, dissociation of mind from body, creative dream-like experiences, and increased perceptual awareness. Other effects include disorientation, confusion, pupillary dilation, and altered time perception, visual and auditory hallucinations, and decreased sexual functioning. Doses of approximately 100-200 mg have a mild, stimulant effect (likened to MDA); doses of 200-500 mg produce a more intoxicating effect (likened to being 'drunk and stoned'); 500-1000 mg may result in mild hallucinations and a mild dissociate effect (likened to a low dose of ketamine) and an overall disturbance in thinking, senses and memory; while doses over 1000 mg may produce a fully dissociative effect (likened to a high dose of ketamine). Abused doses are capable of impairing judgment, memory, language, and other mental performances.

Adverse effects with recommended antitussive doses are rare. However, nausea, other gastrointestinal disturbances, slight drowsiness and dizziness can occur. Following acute doses of between 250-1500 mg, the following clinical and overdose symptoms have been reported: excitation, nausea, vomiting, drowsiness, dizziness, blurred vision, nystagmus, dilated pupils, body itching, rash, ataxia, sweating, hot/cold flashes, fever, hypertension, shallow respiration, urinary retention, diarrhea, opisthotonos (spasm where head and heels are bent back, and torso is bent forward), toxic psychosis (hyperactivity, marked visual and auditory hallucinations), coma, and an increase in heart rate, blood pressure and body temperature. Side effects can be serious if very large doses of the combined preparations are ingested; for example, guaifenesin and dextromethorphan can cause severe nausea and vomiting; chlorpheniramine and dextromethorphan can cause seizure, loss of consciousness and bleeding.

At recommended antitussive doses, addiction does not occur. Mild psychological dependence and depression may occur with regular use of increased doses. Abrupt discontinuation of higher doses may produce insomnia, dysphoria and depression. Poor metabolizers of dextromethorphan have been shown to tolerate lower doses of the drug compared to extensive metabolizers, and report greater sedation, dysphoria and psychomotor impairment. Preliminary evidence also suggests that extensive metabolizers may report a greater dextromethorphan abuse potential due to the increased rate of metabolism to the active metabolite dextrorphan.

Dextromethorphan Hydrobromide was approved in 1957 by the US FDA and the salt is being commercialized through out the world due to the manufacturing convenience. The salt is sparingly soluble below 20° C. (1.5% at 20° C.) while its solubility is high at higher temperature (25% at 85° C.) which makes it easy for crystallization.

While the original approval of Dextromethorphan Hydrobromide by the FDA was intended to use the drug as an antitussive at lower doses for a maximum period of 2 weeks for continuous use, the potential utility of dextromethorphan to relieve chronic pain require the use of the compound in large doses, up to 960 mg/day in a chronic manner which means that the patients would be consuming the drug for months or years everyday (Panitch 2006; Tortella 1989; Steinberg 1996; Sang 2002; Nelson 1997; Gilron 2000; Sindrup 1999; Abraham 2003).

Since bromide was introduced as a medicine, clinical symptoms of bromide intoxication have been reported. Large doses of bromide cause nausea and vomiting, abdominal pain, coma and paralysis. The chronic state of bromide intoxication is reported as bromism. The signs and symptoms are referable to the nervous system, skin, glandular secretions and gastrointestinal tract (van Leeuwen & Sangster, 1988). It was postulated that bromide ion acts directly on certain endocrine organs such as the thyroid, adrenals and testes, thereby inducing alterations in the pituitary gland by feedback mechanisms (van Leeuwen et al., 1983b; Loeber et al., 1983).

In an experiment on the time dependency of the effect of bromide on the thyroid gland in rats, significantly decreased thyroxine concentrations were found as soon as 3 days after feeding diets containing 4800 or 19200 ppm NaBr. This decrease was observed and remained constant during an experimental period of 12 weeks (van Leeuwen et al., 1983a).

In another study, healthy volunteers were repeatedly given sodium bromide in oral doses of 0, 4 or 9 mg Br/kg/day using a double blind design. Groups of seven males received the treatment for 12 weeks and groups of seven non-pregnant females (not using oral conceptives) over three full cycles. Special attention was paid to possible effects on the endocrine and central nervous systems. At the start and end of the study, a full medical history, the results of physical examination, haematological studies and standard clinical chemistry and urine analyses were recorded for each subject. Except for incidental nausea, no changes were observed. Mean plasma bromide concentrations at the end of treatment were 0.07, 2.14 and 4.30 mmol/l for males and 0.07, 3.05 and 4.93 mmol/l for females of the 0-, 4- and 9-mg Br/kg/day groups, respectively. Only in the females receiving 9 mg Br/kg/day was there a significant increase in serum thyroxine and triiodothyronine at the end of the study compared to pre-administration values, but all concentrations remained within normal limits. No changes were observed in serum concentrations of free thyroxine, thyroxine-binding globulin, cortisol, oestradiol, progesterone or testosterone, or of thyrotropin, prolactin, luteinizing hormone (LH) and follicle-stimulating hormone before or after the administration of thyrotropin-releasing hormone and LH-releasing hormone. Analysis of neurophysiological data (EEG and visual evoked response) showed shifts in the power of various spectral bands and a shift in mean frequency in the groups on 9 mg Br/kg/day. All findings were, however, within normal limits (Sangster et al., 1982b; 1983).

A limited replication study was carried out to confirm the findings in the former study. Three groups of 15 females received (double blind) doses of 0, 4 and 9 mg Br/kg/day during three menstrual cycles. After the administration period the 45 females were observed for another three cycles. Mean plasma bromide concentrations at the end of the treatment were 0.07, 3.22 and 7.99 mmol/l, respectively. In none of the three groups were significant changes observed in the serum thyroxine concentration, free thyroxine, triiodothyronine, thyrotropine and thyroxine-binding globulin. Clinical observation did not show effects on the thyroid or on the central nervous system. Quantitative analysis of the electroencephalogram (EEG) showed only a marginal effect in females receiving 9 mg Br/kg/day (Sangster et al., 1986).

After oral ingestion bromide is rapidly and completely absorbed in the gastrointestinal tract and distributed almost exclusively in the extracellular fluid. The similarity of bromide to chloride gives rise to an important pharmacokinetic interaction. The two ions compete for reabsorption in the kidney. High chloride reabsorption will lead to higher bromide excretion and vice versa. The biological half-life of bromide can be decreased by administration of chloride. A normal half-life of bromide in the rat of 3 days will increase to 25 days on a chloride-free diet.

Bromide exerts various toxicological effects in rats. At higher doses, effects on the central nervous system were observed. In short-term toxicity studies motor incoordination of the hind legs and inhibition of grooming were found. The main effects of bromide are on endocrine organs. It is assumed that bromide acts directly on organs such as the thyroid, adrenals and testes, thereby inducing alteration in the pituitary gland by feed-back mechanisms. The effect on the thyroid may be explained by interaction with iodide uptake and is the most sensitive effect in animal experiments.

In a short-term toxicity study with rats at a normal chloride intake, effects were found on most endocrine organs, while in special studies decreased levels of a number of hormones (thyroxine, growth hormone, testosterone and corticosterone) were observed. On the other hand, TSH and insulin were increased. A NOAEL based upon all available data on the effects on the thyroid of 300 ppm sodium bromide (240 ppm bromide), equivalent to 12 mg bromide/kg bw/day could be established.

In a reproduction study in rats, complete infertility was observed at the highest dose level of 19200 ppm sodium bromide whereas at 4800 ppm fertility and viability of the offspring were reduced. At 1200 ppm no effects on reproduction were observed. The effects on fertility were reversible. Bromide was not mutagenic in the Ames test.

U.S. Pat. No. 5,811,547 discloses a method of inducing a transition in crystalline state of a crystallizable medicinal substance with great ease and improved efficiency and uniformity on a high production scale. According to the invention, an extruder is used for inducing a transition from one crystalline state (δ) to another crystalline state in a crystallizable medicinal substance. It claims dextromethorphan hydrochloride among over thousand other chemical entities.

EP application 0921396 discloses methods for rapidly screening subjects for poor and extensive CYP2D6 activity. While the embodiment used only dextromethorphan hydrobromide, the patent claims dextromethorphan hydrochloride for the screening purpose. Radio-labeled dextromethorphan hydrochloride was used in nasal delivery experiments in rats (Char 1992).

Thus, there is a need for an alternative salt of dextromethorphan which can be used for treating chronic diseases such as pain associated with an idiopathic or undiagnosed or an undiagnosible disease, disorder or condition, or pain associated with any one of: myofascial pain syndrome, trigger points, tender points, thorasic outlet syndrome, arachnoiditis syndrome, complex regional pain syndrome (CRPS), reflex sympathetic dystrophy (RSD), sympathetically maintained pain (SMP), diabetic neuropathy syndrome (DNS); chronic pain associated with fibromyalgia syndrome (FMS), trigeminal neuralgia (TN), multiple sclerosis (MS); chronic pain associated with traumatic injury to the peripheral nervous system; chronic pain resulting from herpes zoster (also known as shingles, or post-herpetic neuropathy) or similar infections that attack and damage nerve fibers or endings; post-operative pain, which arises after surgery and then lingers far beyond a normal convalescent period; pain associated with nerve and root damage, such as pain associated with peripheral nerve disorders, including, nerve entrapment and brachial plexus avulsions, amputation, peripheral neuropathies, tic douloureux, atypical facial pain, nerve root damage, and arachnoiditis syndrome, in which an amputee suffers from feelings of pain or discomfort that seems to originate in the missing limb ("phantom limb" pain); pain associated with carcinoma, often referred to as cancer pain; chronic pain associated with chemotherapy treatment; central nervous system pain, including pain due to spinal cord or brain stem damage; lower back pain; sciatica; headache, including migraine, chronic tension headache, cluster headache, temporomandibular disorder (TMJ) pain and maxillary sinus pain; complex regional pain syndromes, including reflex sympathetic dystrophy and causalgia, or from burn injury; the chronic pain associated with hyperesthesia, allodynia, hyperalgesia, deafferentation pain, sympathetically maintained pain, non-nociceptive chronic pain, without the side effect of bromide ion.

SUMMARY OF THE INVENTION

The present invention overcomes limitations in the prior art by providing a dextromethorphan composition which essentially or completely eliminates the risk of bromide toxicity. In particular embodiments, the present invention provides dextromethorphan hydrochloride which may be included in pharmaceutical compositions and used to treat pain.

The invention may be further understood according to the following numbered sentences:
1. A pharmaceutical composition comprising dextromethorphan hydrochloride having the structure:

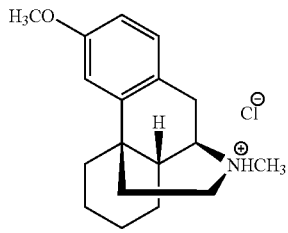

wherein the dextromethorphan hydrochloride is non-radioactive, and wherein the pharmaceutical composition is free or essentially free of bromide.
2. The pharmaceutical composition of sentence 1, wherein the pharmaceutical composition is formulated for oral administration.
3. The pharmaceutical composition of sentence 2, wherein the pharmaceutical composition is a tablet or capsule.
4. The pharmaceutical composition of sentence 2, wherein the pharmaceutical composition is a solution.
5. The pharmaceutical composition of sentence 2, wherein the pharmaceutical composition comprises between 80 mg and 1000 mg or between 15 mg and 200 mg dextromethorphan hydrochloride.
6. The pharmaceutical composition of sentence 2, wherein the pharmaceutical composition is a good manufacturing grade (GMP) pharmaceutical.
7. A method of treating chronic pain comprising administering the pharmaceutical composition of sentence 1 to a subject.
8. The method of sentence 7, wherein the chronic pain results from myofascial pain syndrome, trigger points, tender points, thorasic outlet syndrome, arachnoiditis syndrome, complex regional pain syndrome (CRPS), reflex sympathetic dystrophy (RSD), sympathetically maintained pain (SMP), diabetic neuropathy syndrome (DNS); chronic pain associated with fibromyalgia syndrome (FMS), trigeminal neuralgia (TN), multiple sclerosis (MS), a traumatic injury to the peripheral nervous system, an idiopathic or undiagnosed or undiagnosible disease, a chronic disease, herpes zoster (shingles or post-herpetic neuropathy), an infection which results in damage to nerves, post-operative pain, which arises after surgery and then lingers far beyond a normal convalescent period; pain associated with nerve and root damage, such as pain associated with peripheral nerve disorders, including, nerve entrapment and brachial plexus avulsions, amputation, peripheral neuropathies, tic douloureux, atypical facial pain, nerve root damage, and arachnoiditis syndrome, in which an amputee suffers from feelings of pain or discomfort that seems to originate in the missing limb ("phantom limb" pain); pain associated with carcinoma, often referred to as cancer pain; chronic pain associated with chemotherapy treatment; central nervous system pain, including pain due to spinal cord or brain stem damage; low back pain; sciatica; headache, including migraine, chronic tension headache, cluster headache, temporomandibular disorder (TMJ) pain and maxillary sinus pain; complex regional pain syndromes, including reflex sympathetic dystrophy and causalgia, or from burn injury; the chronic pain associated with hyperesthesia, allodynia, hyperalgesia, deafferentation pain, sympathetically maintained pain, non-nociceptive chronic pain.

DETAILED DESCRIPTION OF THE INVENTION

Figure 1:
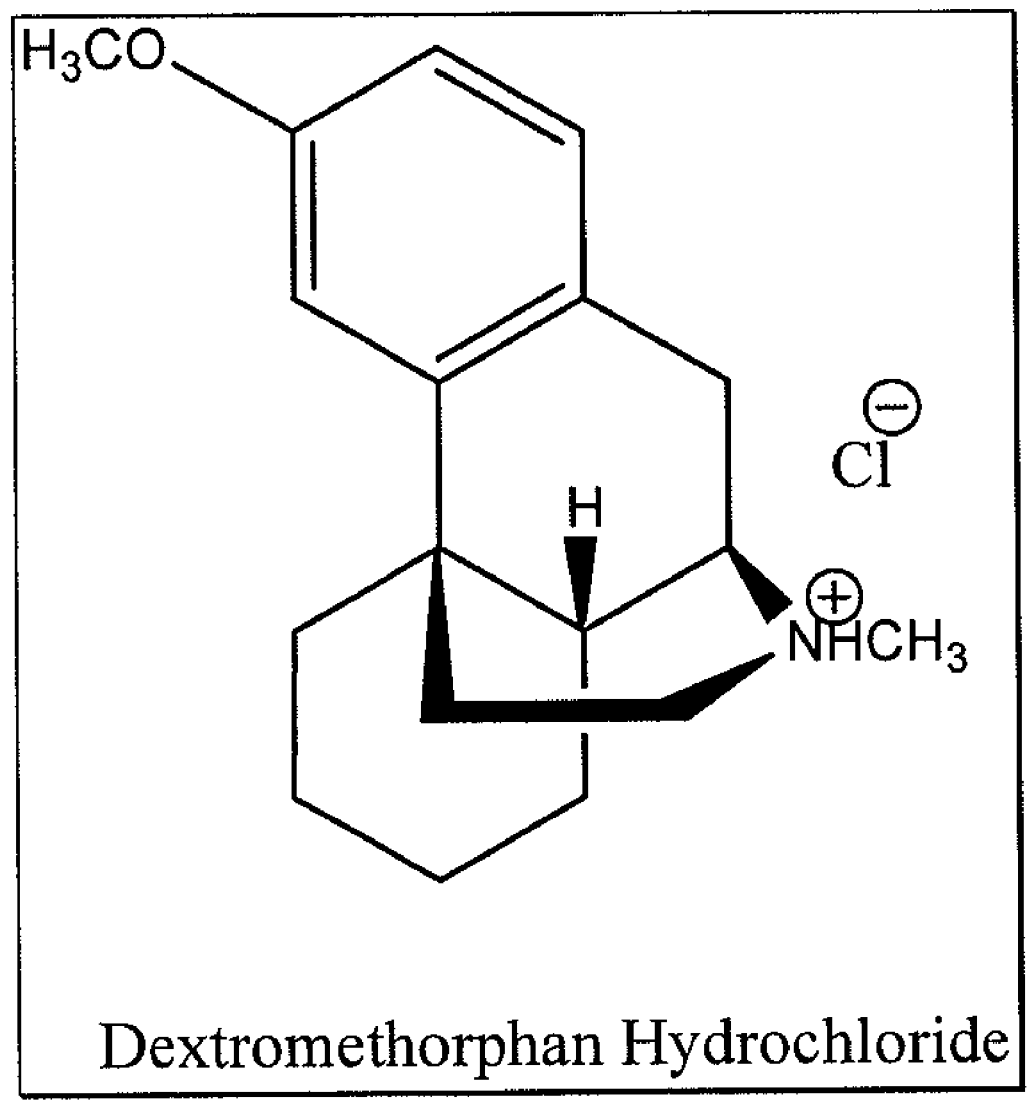
FIG. 1. Chemical structure of dextromethorphan hydrochloride.

The present invention discloses the compound dextromethorphan hydrochloride (FIG. 1) which can be used for treating chronic diseases such as firomyalgia, diabetic neuropathy, chemotherapy induced peripheral neuropathy, post-herpetic neuralgia and phantom pain. The compound of the invention is devoid of bromide ion toxicity due to its replacement by chloride ion.

The chemical name for Dextromethorphan Hydrochloride is 3-methoxy-17-methyl-9a, 13a, 14a-morphinan hydrochloride with the molecular weight of 307.86 and a molecular formula of $C_{18}H_{25}NO.HCl$ Dextromethorphan Hydrochloride is a pure white crystalline powder and has a melting point of 125-128 C. It is freely soluble in water at room temperature and is soluble in alcohol and chloroform. The compound has UV absorption maximum at 278.8 nm and 220 nm.

Dextromethorphan Hydrochloride is prepared by the neutralization of dextromethorphan base in water and purified by recrystallization in water. A method for the preparation is given in Example 1.

The chemical structure of Dextromethorphan Hydrochloride is shown below:

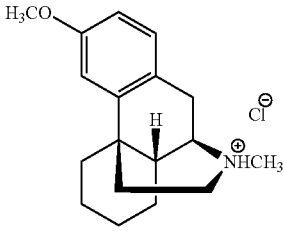

Dextromethorphan Hydrochloride

EXAMPLE 1

Preparation of Dextromethorphan Hydrochloride

The compound was prepared from Dextromethorphan USP and Hydrochloric Acid. A 30 L reactor fitted with stirrer, temperature and pH monitoring system was loaded with 5 Kg of dextromethorphan USP and 20 L of Type I water (17.8 MOhms) and the mixture was stirred so that the powder was uniformly distributed. To this mixture, 1500 mL of concentrated hydrochloric acid was added over a period of 1-2 hours while keeping the temperature of the reaction mixture at 20°-25° C. and monitoring the pH of the mixture. As the chloride salt of dextromethorphan dissolve in water, the mixture became thin as the addition progressed. After the addition, the solution was stirred for 30 minutes and the pH was measured which was above 9.0. Then 350 mL of 1N hydrochloric acid was transferred to the addition funnel and the acid was added slowly to the reaction mixture while stirring, monitoring the pH and maintaining the mixture temperature at 20°-25° C. When the pH of the solution reached around 5-6, the solution was stirred for another 20 minutes and the pH was monitored. The final pH of the solution was adjusted to 5.2 to 5.5. The solution was filtered through a sintered glass funnel and approximately 80% of the water was removed from the solution by rotary evaporation at 50°-60° C. The concentrated solution was transferred to a beaker and left stand at 4 C overnight. The crystals formed were collected in a filtering funnel and dried at 50° C. in a oven under vacuum. The total yield of dextromethorphan hydrochloride was approximately 4.2 KG. The salt was further purified by re-crystallization in water.

I claim:

1. A pharmaceutical composition comprising dextromethorphan hydrochloride having the structure:

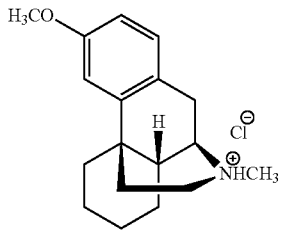

wherein the dextromethorphan hydrochloride is non-radioactive, wherein the said dextromethorphan hydrochloride is in immediate release form; and wherein the pharmaceutical composition is free or essentially free of bromide.

2. The pharmaceutical composition of claim 1, wherein the pharmaceutical composition is formulated for oral administration.

3. The pharmaceutical composition of claim 2, wherein the pharmaceutical composition is a tablet or capsule.

4. The pharmaceutical composition of claim 2, wherein the pharmaceutical composition is a solution.

5. The pharmaceutical composition of claim 4, wherein the pharmaceutical composition comprises between 80 mg and 1000 mg dextromethorphan hydrochloride.

6. The pharmaceutical composition of claim 3, wherein the pharmaceutical composition comprises between 15 mg and 200 mg dextromethorphan hydrochloride.

7. The pharmaceutical composition of claim 2, wherein the pharmaceutical composition is a good manufacturing grade (GMP) pharmaceutical.

8. A method of treating chronic pain comprising administering the pharmaceutical composition of claim 1 to a subject.

9. The method of claim 8, wherein the chronic pain results from myofascial pain syndrome, trigger points, tender points, thoracic outlet syndrome, arachnoiditis syndrome, reflex sympathetic dystrophy (RSD), sympathetically maintained pain (SMP), diabetic neuropathy syndrome (DNS); chronic pain associated with fibromyalgia syndrome (FMS), trigeminal neuralgia (TN), multiple sclerosis (MS), a traumatic injury to the peripheral nervous system, an idiopathic or undiagnosed or undiagnosible disease, a chronic disease, herpes zoster (shingles or post-herpetic neuropathy), an infection which results in damage to nerves, post-operative pain, which arises after surgery and then lingers far beyond a normal convalescent period; pain associated with nerve and root damage, an amputation, peripheral neuropathies, tic douloureux, atypical facial pain, arachnoiditis syndrome, a "phantom limb" pain, a carcinoma or cancer pain, a chemotherapy treatment, central nervous system pain, spinal cord or brain stem damage, lower back pain, sciatica, headache, migraine, chronic tension headache, cluster headache, temporomandibular disorder (TMJ) pain or maxillary sinus pain, a complex regional pain syndrome, a reflex sympathetic dystrophy or causalgia, a burn injury, hyperesthesia, allodynia, hyperalgesia, deafferentation pain, sympathetically maintained pain, or non-nociceptive chronic pain.

* * * * *